(12) United States Patent
Sheleg et al.

(10) Patent No.: US 8,124,329 B2
(45) Date of Patent: Feb. 28, 2012

(54) HYPOTHERMIC PRESERVATION OF BIOLOGICAL TISSUES AND CELLS

(76) Inventors: Sergey V. Sheleg, Scottsdale, AZ (US); Hugh LeRoy Hixon, Jr., Scottsdale, AZ (US); Sergei A. Svarovsky, Scottsdale, AZ (US); Bruce Cohen, Scottsdale, AZ (US)

( * ) Notice: Subject to any disclaimer, the term of this patent is extended or adjusted under 35 U.S.C. 154(b) by 347 days.

(21) Appl. No.: 12/437,291

(22) Filed: May 7, 2009

(65) Prior Publication Data

US 2009/0286220 A1 Nov. 19, 2009

Related U.S. Application Data

(60) Provisional application No. 61/071,730, filed on May 14, 2008.

(51) Int. Cl.
*A01N 1/00* (2006.01)
(52) U.S. Cl. .......... 435/1.3; 435/1.1; 435/325; 424/703; 424/600
(58) Field of Classification Search .................. 435/1.1, 435/1.3; 424/600, 703
See application file for complete search history.

(56) References Cited

U.S. PATENT DOCUMENTS

| 3,729,947 | A | | 5/1973 | Higuchi | |
|---|---|---|---|---|---|
| 4,008,754 | A | * | 2/1977 | Kraushaar et al. | 435/1.3 |
| 5,791,151 | A | | 8/1998 | Verhaag et al. | |
| 6,303,156 | B1 | | 10/2001 | Ferrigno | |
| 2006/0083720 | A1 | * | 4/2006 | Fraser et al. | 424/93.7 |

FOREIGN PATENT DOCUMENTS

RU 2268590 1/2006

OTHER PUBLICATIONS

Poppert et al. Zeitschrift fuer Urologie und Nephrologie (1973) 66(7): 481-8.*
English translation of Poppert et al. Zeitschrift fuer Urologie und Nephrologie (1973) 66(7): 481-8, done Jul. 2011.*
Sheleg et al. Int. J. Clin. Exp. Pathol. (2008; publsihed on-line 30 Nov. 2007) 1: 440-447.*
Robert W. Prehoda, Suspended Animation, The research possibility that may allow man to conquer the limiting chains of time, Chilton Book Company, Philadelphia, New York and London, pp. 81-86, 1969.

* cited by examiner

*Primary Examiner* — Susan Hanley
(74) *Attorney, Agent, or Firm* — Louis Ventre, Jr.

(57) ABSTRACT

A method for hypothermic preservation of biological tissue for later recovery to a viable state includes flushing the biological tissue with a gas mixture of sulfur hexafluoride or xenon and oxygen. The sulfur hexafluoride or xenon is in a concentration in the mixture between about 75 mole percent to 95 mole percent. The method includes pressurizing the biological tissue, preferably isothermically, with the mixture to a pressure that will form clathrates inside the biological tissue at a desired storage temperature in a range of about +1° C. to about +5° C. The method includes a step of cooling the biological tissue, preferably isobarically, to the desired storage temperature. Optional steps for further cooling to no colder than about −20° C. and for depressurization are provided as well as steps for recovering the hypothermically preserved biological tissue to a viable state, preferably using a recovery gas mixture.

8 Claims, 3 Drawing Sheets

FIG.1

```
┌─────────────────────────────────────────────────────────────────────┐
│ A method for recovery to a viable state of biological tissue hypothermically preserved │
│ comprising the steps of:                                            │
│                                                                 200 │
└─────────────────────────────────────────────────────────────────────┘
    │
    │  ┌──────────────────────────────────────────────────────────────┐
    │  │ flushing the biological tissue with a recovery gas mixture consisting of: │
    │  │ helium in a concentration in the recovery gas mixture within a range of 90 │
    │  │ mole percent to 95 mole percent; and, oxygen in a concentration in the │
    │  │ recovery gas mixture within a range of about 5 mole percent to 10 mole │
    │  │ percent; wherein flushing displaces the clathrate inducing gas surrounding │
    │  │ the biological tissue with recovery gas mixture              │
    │  │                                                          210 │
    │  └──────────────────────────────────────────────────────────────┘
    │
    │  ┌──────────────────────────────────────────────────────────────┐
    │  │ subjecting the biological tissue to the recovery gas at a recovery pressure │
    │  │ that permits the clathrate inducing gas to form clathrates inside the cells of │
    │  │ the biological tissue at temperature above zero degrees Centigrade │
    │  │                                                          220 │
    │  └──────────────────────────────────────────────────────────────┘
    │
    │  ┌──────────────────────────────────────────────────────────────┐
    │  │ warming the biological tissue to a first recovery temperature above zero │
    │  │ degrees Centigrade                                           │
    │  │                                                          230 │
    │  └──────────────────────────────────────────────────────────────┘
    │
    │  ┌──────────────────────────────────────────────────────────────┐
    │  │ depressurizing the biological tissue while warming the biological tissue to a │
    │  │ pressure and temperature that restores the tissue to a viable state │
    │  │                                                          240 │
    │  └──────────────────────────────────────────────────────────────┘
    │
    │  ┌──────────────────────────────────────────────────────────────┐
    └──│ flushing takes place at a pressure within a range of 100 pounds per square │
       │ inch absolute to 120 pounds per square inch absolute         │
       │                                                          250 │
       └──────────────────────────────────────────────────────────────┘
```

HYPOTHERMIC PRESERVATION OF BIOLOGICAL TISSUES AND CELLS

CROSS REFERENCE TO RELATED APPLICATIONS

This application claims the benefit of U.S. Provisional Application 61/071,730, filed May 14, 2008, which is hereby incorporated by reference herein.

TECHNICAL FIELD

The present invention encompasses a method of hypothermic preservation of biological tissue in a viable state in a controlled process of refrigeration in the presence of a chemical agent that minimizes cellular damage from refrigeration.

BACKGROUND ART

Biological tissue, or simply tissue, as used herein includes a plurality of cells or any cellular material that carry out a biological function. Any plant or animal tissue is included. Animal organs or whole animals, such as Planaria, are included. The cells are not necessarily identical, but are preferably of the same origin.

The primary storage mechanism employed in this invention uses tissue storage temperatures above zero degrees Centigrade, (i.e., above the freezing point of water at atmospheric pressure) in the presence of a gaseous chemical agent. The tissue remains viable in long or short term storage, essentially hibernating with significantly reduced biological function. The process enables the tissue to be later recovered to a viable state, that is, to a state with normal biological function.

The present invention can also be employed for biological tissue storage in a specific range of below freezing temperatures using this same gaseous chemical agent. These embodiments also maintain a viable tissue that is capable of restoration of normal tissue function when recovered to above freezing temperatures.

Conventional processes that seek to preserve tissue at low temperatures include near-freezing storage; conventional vitrification, and conventional cryopreservation. None teaches the process of the present invention and all suffer from overall inadequate performance in viable storage and recovery to a state of normal function.

Lowering the temperature as a preservative of biological tissue is known in the art. See for example U.S. Pat. No. 5,791,151 which uses a near-freezing temperature in an oxygen environment. However, sustaining viability of tissue and recovering the tissue to normal function with the teachings in the prior art is problematic.

Prior art processes typically use liquid polar organic compounds in solution to perfuse the biological tissue. These conventional processes are not reversible in that they cannot be used to restore tissue to life, although occasional exceptions are observed in nature that involve, for example, vitrifying polyols (i.e., insects, amphibians) or thermal hysteresis proteins (insects, fish). See, Fletcher G L, Hew C L and Davies P L, Antifreeze proteins of teleost fishes. Annu Rev Physiol, 63 (2001) 359-590; Graham L A, Liou Y C, Walker V K and Davies P L, Hyperactive antifreeze protein from beetles. Nature, 388 (1997) 727-728. The present method does not employ a liquid, but rather employs a specific gaseous chemical agent in a specific process that enhances the viability of biological tissue in short and long-term storage and enhances recovery of that tissue when required.

Near-freezing storage seeks to preserve organs by lowering their temperature near to the freezing point of water. See, e.g., U.S. Pat. No. 7,029,839. Near-freezing storage involves perfusing the tissue with an aqueous solution containing protectants that depress the freezing point of the solution, so that the tissue may be stored at low temperature with aqueous fluids in the cells in a liquid state. Examples of liquid polar organic compounds used as conventional protectants are dimethyl sulfoxide, glygerol, ethylene glycol, and propylene glycol. Conventional protectants can function by binding water through a combination of hydrophilic and hydrophobic interactions at different points on the molecule.

Conventional protectants can present problems when used on larger pieces of tissue; such problems are generally attributed to the nonuniform distribution of the protectants within the tissue. Conventional protectants typically diffuse slowly and pass through cell membranes and the blood-brain barrier poorly or not at all. Furthermore, large quantities of protectants may be required.

Typically, conventional protectants bind with about two moles of water per mole of protectant. When used in the required quantities to bind water conventional protectants may be toxic to cells. The near-freezing storage process is slow and requires that high concentrations of potentially harmful protectant chemicals be introduced to and removed from the tissue.

In general, preserving biological tissue by lowering its temperature below freezing is destructive of cellular tissue when crystalline ice forms within the cells (intracellular) and around cells (extracellular) as the liquid water within the biological tissue transitions to the solid phase (ice). The mechanism of freezing damage in living tissue is principally due to two processes.

The first process causing freezing damage involves the formation of ice in the intercellular spaces. The vapor pressure of the ice is lower than the vapor pressure of the solute water in the surrounding cells and as heat is removed at the freezing point of the solutions, the ice crystals grow between the cells, extracting water from them. As the ice crystals grow, the volume of the cells shrinks, and the cells are crushed between the ice crystals.

The second process causing freezing damage involves the concentration of solutes inside the water remaining in the cells as the cells shrink. The increased concentration of solutes increases the intracellular ionic strength and interferes with the organization of proteins and other intercellular structures. Eventually, the solute concentration inside the cells reaches the eutectic and freezes. The final state of the frozen tissue is pure ice in the extracellular spaces, and a mixture of concentrated cellular components in ice and bound water inside the cells.

Most lesions in tissue occur during re-warming and reperfusion of cryopreserved biological tissues, such as organs; the process of its development is time-consuming. Changes include condensation of chromatin, large lipid droplets, and partly disrupted plasma membrane; these changes may be seen on electron microscopy (which may be a consequence of the osmotic excursions incurred during a freeze-thaw cycle; leakage of mitochondrial matrix can trigger apoptosis as well).

Damage to biological tissue by freezing is caused, besides temperature stress owing to decrease in temperature itself, by the following processes: irreversible change of biological membrane by dehydration from the cells and surface of the membranes caused by the freezing process; destruction by loss in selective permeability; and, physical deformation and death of the cell. Light microscopy does not show early freezing damage to the cells. The present invention avoids such damage.

Conventional vitrification involves the use of a conventional cryoprotectant solution and cryogenic temperatures. See, e.g., U.S. Pat. No. 4,559,298. A concentrated aqueous cryoprotectant solution can permit solidification without the formation of ice crystals. That is, vitrification can involve inducing the transition of an aqueous liquid to an amorphous solid phase in both the intracellular and the extracellular spaces of tissue by cooling to a cryogenic temperature with the use of a conventional cryoprotectant, such as glycerol. However, vitrification requires the impregnation of biological tissues with high concentrations of toxic cryoprotective chemicals that promote the vitreous state.

Although vitrification can avoid ice formation, alternative potential mechanisms of injury associated with the amorphous state have been identified. Devitrification (ice formation in biological tissues during re-warming) is a major obstacle to successful organ vitrification and subsequent recovery. Vitrification has failed to successfully preserve and return to a viable state mammalian internal organs.

Conventional cryopreservation can involve the use of liquid cryoprotectant solutions to prevent intracellular ice crystal formation, while allowing ice crystals to form in extracellular areas. In addition to using potentially toxic protectant chemicals, conventional vitrification and conventional cryopreservation techniques can cause cells to undergo volume changes during vitrification or freezing, which results in mechanical stresses sufficient to cause cracking and cell destruction.

The use of xenon in cryopreservation was discussed by P. V. Shcherbakov and V.1. Telpuhov. See, P.V. Shcherbakov and V.1. Telpuhov, Chemistry and Life, v.8 (2006) pp. 34-39 (in Russian). Additionally, Russian patent RU2268590 to Shcherbakov, et al. (published Jan. 27, 2006 with English language Abstract) discusses saturating tissue with a mixture of xenon, krypton, and argon, forcing water out of the tissue with this mixture of noble gases under pressure while cooling to −43° C., and decreasing the pressure to ambient pressure and continuing to cool to −196° C. The present invention does not employ cryopreservation temperatures as taught by Shcherbakov. The pressure of the noble gas mixture presented in the Shcherbakov publications does not allow for sufficient water to be bound in the cells to allow for rehydration sufficient for metabolism to restart. The present invention utilizes a specific gas mixture and a specific concentration not taught in the Shcherbakov publications. Further, the Shcherbakov publications do not present a method suitable for viably storing tissue capable of recovery to a viable state as enabled in the present invention.

SUMMARY OF THE INVENTION

A method for hypothermic preservation of biological tissue for later recovery to a viable state is described. The method involves a step of flushing the biological tissue to displace the gases in the environment surrounding the biological tissue. The flushing gas is a gas mixture of sulfur hexafluoride or xenon and oxygen. The sulfur hexafluoride or xenon is in a concentration in the mixture in a range of about 75 mole percent to 95 mole percent. The method includes a step of pressurizing the biological tissue with the gas mixture to a pressure that will form clathrates inside the biological tissue at a desired storage temperature in a range of about plus one degree Centigrade to about plus 5 degrees Centigrade. This pressure is in a range from about 75 to 100 psig (121) and is preferably attained while maintaining the biological tissue at approximately the same temperature, that is, isothermically (122). The method includes a step of cooling the biological tissue to the desired storage temperature and is preferably cooled while maintaining the biological tissue at approximately a constant pressure, that is, isobarically.

Optional steps may be employed of further cooling the biological tissue to a second desired storage temperature warmer than about minus 20 degrees Centigrade and then depressurize the biological tissue. The second desired storage temperature is one at which clathrates would form and remain in the tissue from the clathrate inducing gas at a second storage pressure between about 15 pounds per square inch gauge, and 100 pounds per square inch gauge. Depressurization is preferably to atmospheric pressure of about 15 pounds per square inch gauge (151).

The invention optionally includes two further steps for recovering the biological tissue from the hypothermically preserved state. One such step includes flushing the biological tissue to remove the gas mixture. Flushing is performed with a recovery gas mixture of a first component selected from a group consisting of helium, a noble gas, nitrogen, and a combination of these; and, oxygen. The first component is at a partial pressure of about 90 pounds per square inch in the mixture. A second such step includes warming the biological tissue to a recovery temperature that restores the tissue to a viable state.

ADVANTAGEOUS EFFECTS OF THE INVENTION

Hypothermic preservation according to the present invention preserves the biological tissue in a viable state and enables reheating the biological tissue to restore the function of the tissue under its normal functioning temperature and pressure.

Hypothermic preservation according to the present invention is simple compared with less functional methods that require the use of a cryopreservation solution.

Hypothermic preservation according to the present invention is inexpensive in comparison with less functional conventional vitrification processes which use expensive chemicals like synthetic ice blocking compounds.

Hypothermic preservation according to the present invention is not toxic for biological specimens, in contrast with conventional cryopreservation and vitrification processes.

Hypothermic preservation of biological tissues according to the present invention may be used to preserve biological samples for which no conventional method of long-term preservation exists, such as human blood components for transfusion, such as human blood platelets, and human organs for transplantation, such as hearts, kidneys, and livers. Other applications of hypothermic preservation of biological tissue include the high-quality preservation of food, such as seafood.

BRIEF DESCRIPTION OF DRAWINGS

The drawings show preferred embodiments of the invention.

DESCRIPTION OF EMBODIMENTS

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts may be employed and other methods developed without parting from the spirit and scope of the invention.

The present invention encompasses a method for short- and long-term hypothermic preservation of biological tissues and cells that employ a gas mixture that sequesters some water in cells in a gas hydrate clathrate as cells are cooled, making the water unavailable to form ice crystals in the extracellular space.

Figure 1:
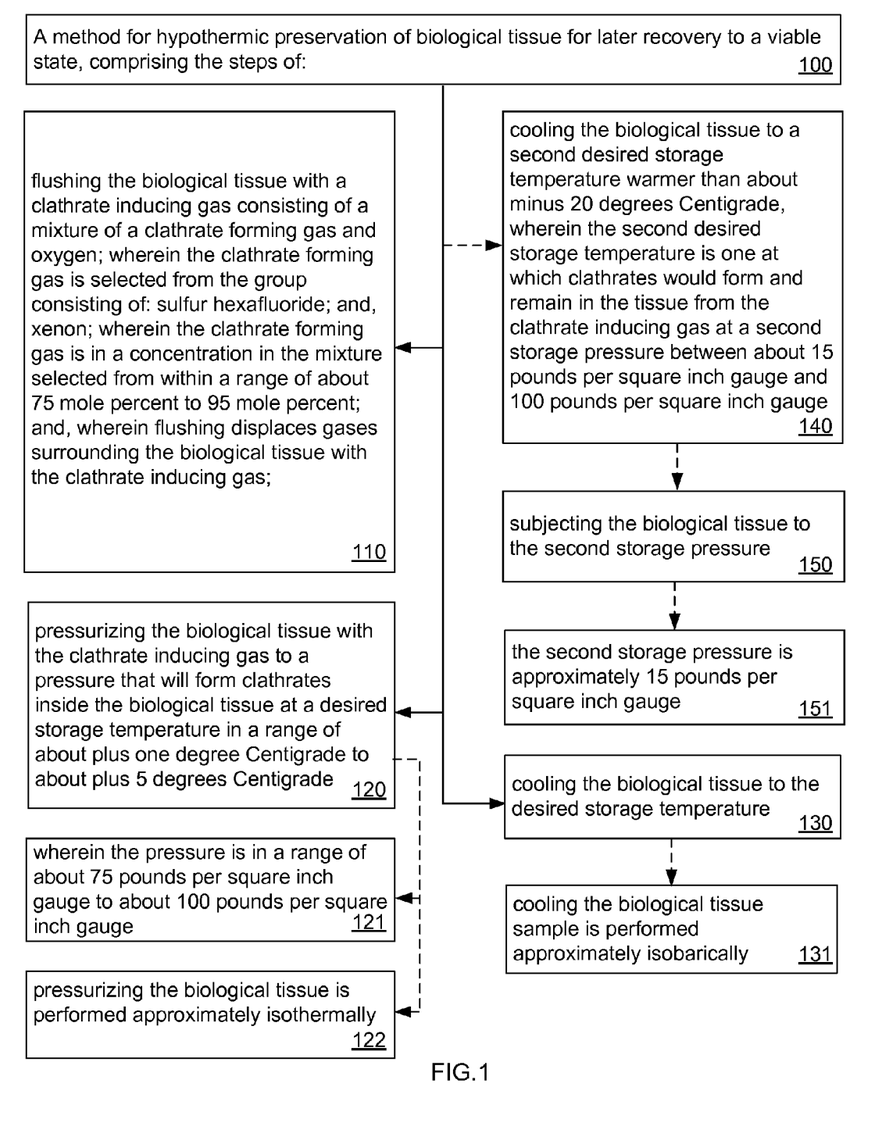
FIG. 1 illustrates preferred embodiments of the process of hypothermic preservation of biological tissue in accordance with the invention.

FIG. 1 illustrates preferred embodiments of the process of hypothermic preservation of biological tissue in accordance with the invention. The solid connecting lines connect necessary steps and the dashed connecting lines connect optional steps.

The box designated (100) explains that the invention is a process or method for hypothermic preservation of biological tissue for later recovery to a viable state. The invention includes a plurality of steps, which, when the context permits, may be performed in any order.

A flushing step (110) includes flushing the biological tissue with a clathrate inducing gas consisting of a mixture of a clathrate forming gas and oxygen. The clathrate forming gas is either sulfur hexafluoride or xenon. The clathrate forming gas is in a concentration in the mixture between about 75 mole percent to 95 mole percent. The flushing displaces gases surrounding the biological tissue with the clathrate inducing gas.

Herein, the term "clathrate forming gas" includes xenon or sulfur hexafluoride. It is these two specific gases that have been tested and provide the desired result of forming a gas hydrate clathrate under the conditions designated for the invention.

The term "clathrate inducing gas" includes a mixture of either of the two clathrate forming gases (xenon or sulfur hexafluoride) and oxygen. Thus, "clathrate inducing gas" includes a mixture of xenon and oxygen or a mixture of sulfur hexafluoride and oxygen. Sulfur hexafluoride may have advantages over xenon as the clathrate-forming gas. For example, sulfur hexafluoride is less expensive than xenon. This may allow for hypothermic preservation of biological tissue using sulfur hexafluoride on a larger scale than is practical for hypothermic preservation using xenon. Sulfur hexafluoride may be safer to use than xenon, because sulfur hexafluoride does not induce narcosis at some concentrations as might be expected with xenon.

More specifically, the clathrate inducing gas used to perform the invention must be in a concentration in the mixture selected from within a range of about 75 mole percent to 95 mole percent. The oxygen therefore preferably comprises the remainder of the mixture and is therefore preferably in a concentration of 25 mole percent to 5 mole percent, respectively.

For example, the biological tissue may initially be flushed with a clathrate inducing gas that includes about 21 mol % oxygen and about 79 mol % sulfur hexafluoride. In this way, the partial pressure of oxygen imposed on the sample by the clathrate inducing gas is the same as the partial pressure of oxygen in the Earth's atmosphere at sea level. Using oxygen in the clathrate inducing gas at a concentration that is the same or similar to that of Earth's atmosphere at sea level may help avoid potential damage to the sample caused by a hypoxic environment.

In a gas hydrate clathrate, a molecule of gas is enclosed by a cage-like structure of water molecules having a structure somewhat like a five-sided honeycomb. Some alternative names for clathrates in which water is the host species are aqueous clathrates, water clathrates, and clathrate hydrates.

In a gas hydrate clathrate, the water molecules are linked through hydrogen bonding and create a host lattice (i.e. the honeycomb cavities). There is no chemical bonding between the host water molecules and the enclosed molecule of gas. Examples of other known clathrate forming gases include the noble gases argon (Ar), krypton (Kr), nitrogen (N), some non-polar gases, some haloalkanes, some hydrofluorocarbons, trifluoromethane, fluoroform, R-23, HFC-23, bromotrifluoromethane, Freon FE 1301, tetrafluoroethane, and R134a.

The clathrate forming gases used in the present invention are sulfur hexafluoride or xenon. The use of xenon or sulfur hexafluoride in the present invention enables the formation of gas hydrate clathrates at moderate pressures and temperatures, which is a probably a result of their high molecular weight and rather strong associated van der Waal's forces. For the present invention, these gases have been found to be non-toxic when combined with oxygen. They are also desirable because they have been found to rapidly penetrate into biological tissue.

The oxygen in the mixture permits metabolic activity in hypothermically stored biological tissue. Oxygen is also useful when taking preserved biological tissue out of hypothermic storage, i.e., recovering biological tissue by increasing its temperature to room temperature with the intention of restoring normal metabolic activity, i.e., life functions.

The term "viable" means capable of living. For example, tissue hypothermically preserved according to an embodiment of the present invention may be referred to as viable. Although the tissue in its hypothermically preserved state, for example may exhibit little detectable metabolism, the tissue may be recovered by returning it to conditions, for example, room temperature, e.g., +20° C., at which the tissue exhibits normal metabolism.

The function of the flushing step (110) is to displace gases in the environment surrounding the biological tissue with the clathrate inducing gas. The biological tissue will preferably be in an apparatus suitable to enable performance of the steps of the invention. This will typically be in a container of some kind presenting a closed environment and, thus, the biological tissue may be surrounded by atmospheric gases (air) or may be surrounded by other gases. The flushing step (100) clears the environment surrounding the biological tissue of gases other than the clathrate inducing gas.

FIG. 1 next shows a pressurizing step (120), which includes pressurizing the biological tissue with the clathrate inducing gas to a pressure that will form clathrates inside the cells of the biological tissue at a desired storage temperature in a range of about plus one degree Centigrade to about plus five degrees Centigrade.

Figure 3:
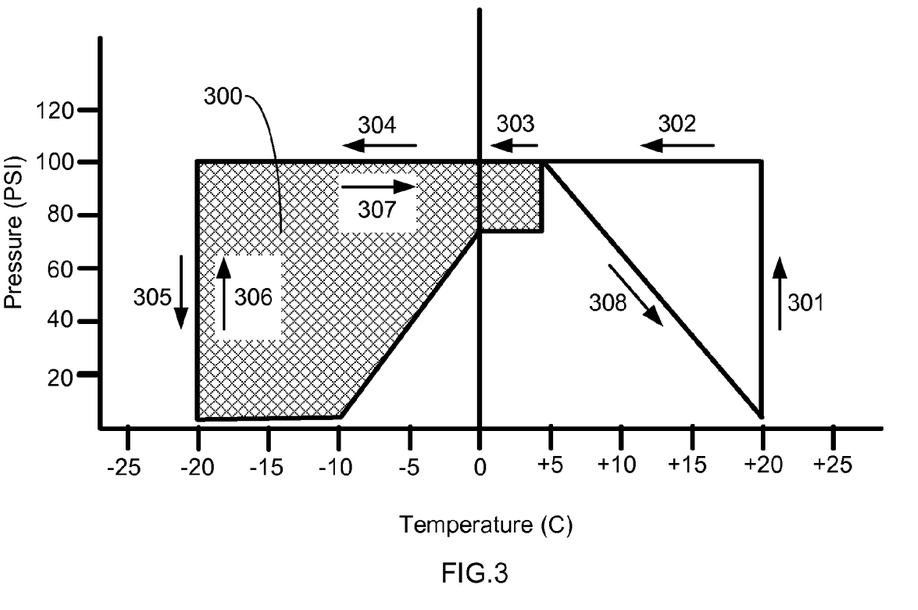
FIG. 3 presents a graph of pressure versus temperature that illustrates process steps for hypothermic preservation and recover of a biological tissue according to the invention.

This pressurizing step (120) is best explained with reference to FIG. 3, which is a graph of pressure versus temperature and which shows the pressure and temperature conditions required for the clathrate inducing gas to be in a clathrate forming region (300), represented by the cross-hatched area in FIG. 3. In these temperature and pressure conditions the clathrate inducing gas forms a clathrate with the water in the biological tissue. FIG. 3 also illustrates preferred process steps shown by the numbered arrows for hypothermic preservation and recover of a biological tissue according to the invention.

The non-cross-hatched region in the graph illustrates where the clathrate inducing gas is present as a gas and water is present as a liquid or as a solid (ice). For example when using sulfur hexafluoride as the clathrate forming gas, the phase boundary between the sulfur hexafluoride hydrate clathrate phase and the sulfur hexafluoride gas-water mixture phase is the border of the shaded region running approximately diagonally from the lower left to the upper right. As indicated by this phase boundary, as temperature decreases, the pressure required to effect a phase change from a sulfur hexafluoride gas-water mixture to a sulfur hexafluoride hydrate clathrate also decreases.

The pressurizing step (120) is preferably performed isothermically and so isothermal pressurization is illustrated by the arrow (301) at a typical ambient temperature of 20 degrees Centigrade. A pressure that will form clathrates inside the cells of the biological tissue at a desired storage temperature in a range of about plus one degree Centigrade to about plus five degrees Centigrade is shown in FIG. 3 as between about 75 pounds per square inch gauge and 100 pounds per square inch gage. This is the same as about 90 pounds per square inch absolute and 115 pounds per square inch absolute.

It is possible to perform the pressurizing step (120) such that the concentration of the clathrate inducing gas is changed as pressure is increased on the biological tissue. This implementation would not keep the partial pressure of oxygen approximately constant and this is not preferred. Rather, it is preferable that the partial pressure of oxygen in the clathrate inducing gas that is imposed on the biological tissue remain approximately constant as the pressure acting on the biological tissue is increased. For example, if clathrate inducing gas is added to increase the total pressure to 100 pounds per square inch gauge (115 pounds per square inch absolute), then the partial pressure of sulfur hexafluoride or the xenon at the end of this step will be about 112 pounds per square inch absolute, while the partial pressure of oxygen remains at about 3 pounds per square inch absolute. Maintaining the partial pressure of oxygen imposed on the sample approximately constant at the partial pressure of oxygen in Earth's atmosphere at sea level will help to avoid potential damage to the biological tissue caused by a hyperoxic environment or oxygen toxicity.

FIG. 1 next shows a cooling step (130), which is cooling the biological tissue to the desired storage temperature. The cooling step (130) is preferably performed isobarically, and so isobaric cooling is illustrated by the arrow (302) at the approximate maximum pressure of about 100 pounds per square inch gage. The desired temperature range of about one degree Centigrade to about plus five degrees Centigrade is illustrated under the arrow (303).

The rate of cooling of the biological tissue may be selected and is not limited by the invention. A preferable range of cooling rates in a range of from +20° C. to +50° C. over a duration from about 15 minutes to about 120 minutes. Selection of a rate of cooling may be influenced by a number of factors. For example, a fast rate of cooling may be selected for a small sample because a small sample of biological tissue would rapidly adjust to the temperature imposed at the wall of the pressure chamber. In another example, a slow rate of cooling might be selected for a large sample, such as a whole organ such as a heart or kidney, because a comparatively long time would be required for a region in the interior of the sample to cool to the desired storage temperature. It is preferable to cool at a rate which permits the biological tissue to maintain approximately a uniform temperature throughout the biological tissue.

FIG. 1 also shows optional steps that may be added to the above described steps.

A further cooling step (140) may be added, which involves cooling the biological tissue to a second desired storage temperature warmer than about minus 20 degrees Centigrade, wherein the second desired storage temperature is one at which clathrates would form and remain in the tissue from the clathrate inducing gas at a second storage pressure between about 15 pounds per square inch gauge and 100 pounds per square inch gauge. This further cooling step (140) is best explained with reference to FIG. 3. The clathrate forming region (300) is shown as a cross-hatched area approximately to the left of the zero temperature line represents the temperature and pressure conditions within which the biological tissue may be taken in compliance with this further cooling step (140). The further cooling step (140) is represented by the arrow (304), which may be performed with varying pressure. However, this further cooling step (140) is preferably performed isobarically (131). As can be seen from FIG. 3, the minimum temperature in compliance with this step is about minus 20 degrees Centigrade. Also, in reference to FIGS. 1 and 3, if the second storage pressure is about atmospheric pressure, that is, about 15 pounds per square inch gauge (151), then the warmest that second desired storage temperature compliant with the limitations in this step may be is about minus 10 degrees Centigrade.

When implementing the optional further cooling step (140), a second pressurization step (150) is required and that is subjecting the biological tissue to the second storage pressure. While it is possible to set the second storage pressure at about the same value as the desired storage pressure attained with above freezing temperatures, it is anticipated that storage at a lesser pressure, such as atmospheric pressure, would be preferable for long time periods. This step is represented by the arrow (305) in FIG. 3.

However, this second pressurization step (150) is phrased so as to require subjecting the biological tissue to the pressure, rather than stating a depressurization or pressurization step. This would accommodate a situation, for example, where the above freezing storage pressure was 80 pounds per square inch gauge and the second storage pressure was 100 pounds per square inch gauge. It would also accommodate a situation where the above freezing storage pressure was 100 pounds per square inch and the second storage pressure was 80 pounds per square inch.

Optionally, but preferably, before conducting the optional further cooling step (140), the temperature and pressure imposed on the biological tissue when first cooled are maintained approximately constant for a period of time (isothermal and isobaric conditions). This period of time is a duration over which a large part of the clathrate structure that can form within the biological tissue is formed within the biological tissue. For example, this period of time might be selected as the duration required for 90% of the water available for incorporation in a clathrate to be incorporated in a clathrate. This period of time may be selected on the basis of theoretical or empirical models of the kinetics of clathrate formation and/or by an iterative trial-and-error process conducted on trial samples having the same or similar composition as the biological tissue that is to be hypothermically preserved. For example, such period of time might be selected to be in a range of from about 15 minutes to about 120 minutes.

Figure 2:
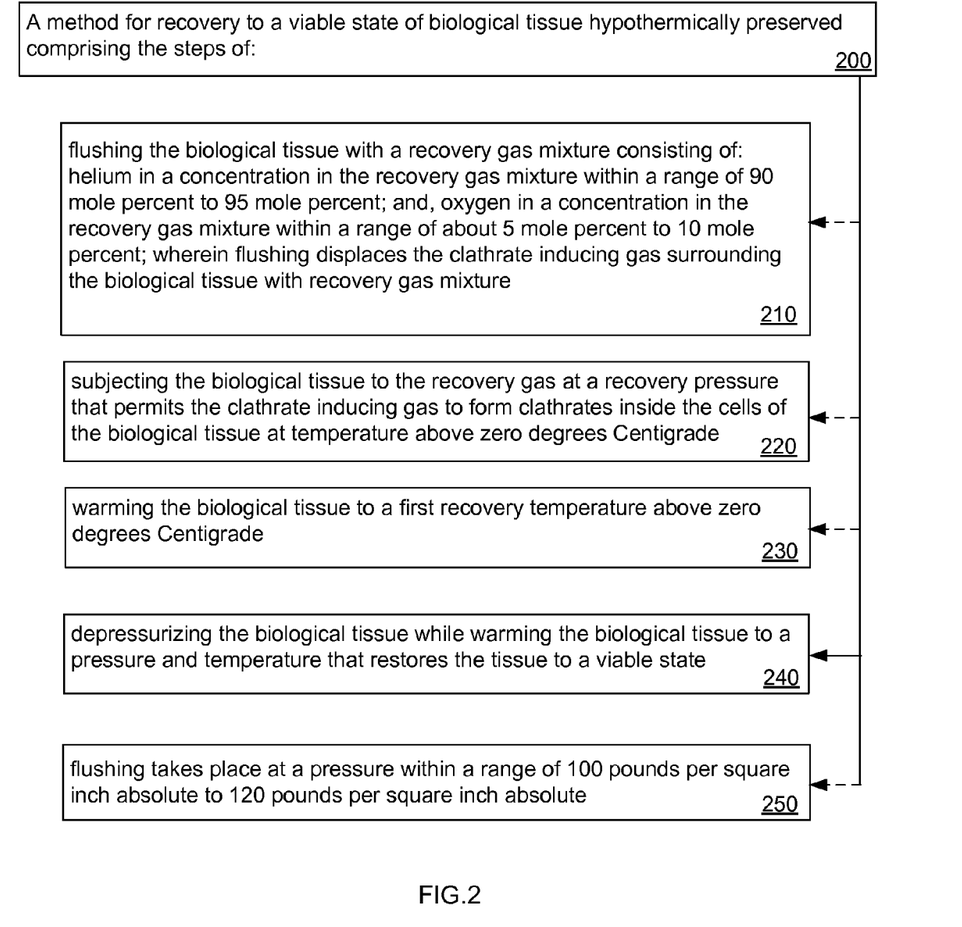
FIG. 2 illustrates preferred embodiments of the process of recovery of biological tissue hypothermically preserved in accordance with the invention.

Recovery steps are shown in FIG. 2. These are steps that would be added to the hypothermic preservation steps for recovery of the biological tissue to a viable state (200). Reference is also made to FIG. 3.

The simplest recovery method for hypothermic storage above freezing (zero degrees Centigrade) is one recovery depressurizing step (240) involving depressurizing the biological tissue while warming the biological tissue to a pressure and temperature that restores the tissue to a viable state.

The best method for recovery of biological tissue involves a recovery flushing step (210) comprising flushing the biological tissue with a recovery gas mixture consisting of helium and oxygen. The helium is in a concentration in the recovery gas mixture within a range of 90 mole percent to 95 mole percent. The oxygen is in a concentration in the recovery gas mixture within a range of about 5 mole percent to 10 mole percent. Flushing displaces the clathrate inducing gas surrounding the biological tissue with recovery gas mixture and permeates the biological tissue, which prevents the biological tissue from abrupt clathrate break-up during the recovery step.

For recovery of biological tissue stored above freezing (zero degrees Centigrade), flushing preferably takes place at a pressure within a range of 100 pounds per square inch absolute to 120 pounds per square inch absolute (240).

For recovery of biological tissue stored below freezing, flushing preferably takes place at a pressure that maintains the biological tissue within the clathrate forming region (300) defined by the cross-hatched area in the phase diagram of FIG. 3. Thus, a subjecting step (220) is subjecting the biological tissue to the recovery gas mixture at a recovery pressure that permits the clathrate inducing gas to form clathrates inside the cells of the biological tissue at temperature above zero degrees Centigrade.

At the start of the recovery process, the biological tissue contains gas hydrates from the clathrate inducing gas. Thus, it is preferable that the recovery process be performed under temperature and pressure conditions that maintain the gas hydrates during the warming process to an above freezing temperature. In this manner, formation of water ice at below freezing temperatures will be prevented. Thus, prior to warming the biological tissue, it should be subjected to a pressure that will maintain the biological tissue in the clathrate forming region (300) shown in the cross-hatched area of FIG. 3.

In colder than freezing storage, the biological tissue may stored at temperatures between minus 10 and minus 20 degrees Centigrade and thus may be at any storage pressure between about atmospheric pressure and about 100 pounds per square inch gauge. In reference to FIG. 3, it can be readily seen that in order that the biological tissue remain at temperature and pressure conditions in the clathrate forming region (300) during the warming process to an above zero degrees Centigrade temperature, the biological tissue must be subjected to recovery gas mixture at a pressure between about 75 pounds per square inch gauge to about 100 pounds per square inch gauge.

For example, if the second storage pressure is at atmospheric pressure, then the biological tissue would be repressurized with the recovery gas mixture to a pressure in a range of approximately 75 pounds per square inch gauge to 100 pounds per square inch gauge. Alternatively if the second storage pressure is 100 pounds per square inch gauge, then the tissue may be subjected to a recovery gas mixture at the same pressure, or at any pressure between about 75 pounds per square inch gauge to 100 pounds per square inch gauge. This subjecting recovery step (220) may be performed isothermically and is shown in FIG. 3 as arrow (306).

Once the biological tissue is subjected to the recovery pressure, a first warming recovery step (230) involves warming the biological tissue to a first recovery temperature above zero degrees Centigrade. This step may be performed isobarically and is shown in FIG. 3 as arrow (307).

Preferably, the first recovery temperature is between about one degree Centigrade and about five degrees Centigrade, which remains in the clathrate forming region, but the first recovery temperature may be at any above freezing temperature that maintains a viable biological tissue. FIG. 3 illustrates the case where the first recovery temperature is at about 5 degrees Centigrade when the preferred depressurizing step (240) indicated by arrow (308) begins.

The rate of warming to the first recovery temperature may be selected. For example, the rate of warming might be in a range of from about 1° C. per hour to about 20° C. per hour. An example of factors to be considered when selecting the rate of warming is the rate of heat conduction through the sample and/or the size of the sample. For example, a relatively high rate of warming may be selected for a sample through which heat conducts rapidly and/or that is small. For example, a relatively low rate of warming may be selected for a sample through which heat conducts slowly and/or that is large. The rate of warming may be selected, so that the temperature throughout the biological tissue is relatively constant. Warming of the biological tissue may be achieved by, for example, by conduction, e.g., by increasing the temperature of the gas surrounding or circulating about the sample or increasing the temperature of a wall of a pressure chamber where the process may be carried out.

A higher rate of warming of the sample while maintaining a similar temperature throughout the sample may be achieved by radiatively heating the sample or using combined radiation and conduction to heat the sample. For example, microwaves may be used to heat the sample. The microwaves can penetrate into the sample to produce heat in the interior of the sample, rather than heat only traveling from the surface of the sample into the interior as with heating by conduction from the wall of the pressure chamber or the surrounding gas. For example, infra-red radiation may be used. Whether radiation is selected for heating the sample, the type of radiation, e.g., microwave or infrared, and the characteristics of the radiation, e.g., wavelength depends on evaluation of a number of factors, such as transparency of regions, e.g., outer layers, of the sample to the radiation and absorbance of regions, e.g., inner regions, of the sample to the radiation.

The preferred depressurizing step (240) involves depressurizing the biological tissue while warming the biological tissue to a pressure and temperature that restores the tissue to a viable state.

Alternatively, the recovery process could warm isobarically and then depressurize to atmospheric conditions in two steps. However, controlling the pressure while warming is an unnecessary complication of the process.

The rate of decrease of pressure and the variation of temperature with decreasing pressure (if temperature is increased while decreasing pressure) may optionally be selected based on a number of factors. For example, the rate of decrease of pressure may be selected to allow gases dissolved in the sample to migrate out of the sample without forming bubbles or with the formation of only small bubbles, with the goal of avoiding the formation of gas bubbles of a size that may damage the sample. If temperature is increased while pressure is decreased, the change in solubility of the gases in the tissue with increased temperature may be considered. The change in solubility of the gases in the tissue with increased temperature may also affect the choice of variation in temperature with decreasing pressure. The selection of the rate of decrease in pressure and/or variation in temperature with decreasing pressure may be guided by theoretical or empirical models, for example, diving decompression tables or by trial-and-error experimentation on trial samples.

After the preferred depressurizing step (240), the biological tissue may be returned to an environment of atmospheric gases.

When above freezing hypothermic storage is utilized, the recovery method is similar. The same steps as described above for below freezing storage are involved, except there is no need for a first warming recovery step (230) because the biological tissue is already above freezing. Thus, the recovery flushing step (210); the subjecting recovery step (220); and, the preferred depressurizing step (240) are performed when above freezing hypothermic storage is utilized.

EXAMPLE 1

Hypothermic Preservation of Tissue with Xenon Hydrate Clathrates

Experiments were performed on 10 albino mice (Mus musculus) (male, 6-8 weeks old; 25±2 gm body weight). The animals were euthanized with Halothane (Sigma-Aldrich; Cat. #B4388) (according to the procedures recommended by the Panel on Euthanasia of the American Veterinary Association) and the hearts were immediately dissected and put into CORNING® vials (without the caps) containing 200 lll of oxygenated modified Krebs-Henselite solution (118.4 mM NaCl, 25 mM NaHCO$_3$, 4.7 mM KCl, 1.6 mM KH$_2$PO$_4$, 0.6 mM MgSO$_4$, 2.5 mM CaCl$_2$, 11 mM glucose) to protect the cardiac tissue from drying. Cardiomyocytes serve as a model to study dynamics of mitochondrial damage in clinical and experimental pathology.

The vials were put inside a pressure chamber, pressurized with xenon-oxygen mixture (90 pounds per square inch xenon; 10 pounds per square inch oxygen) and left on ice for 15 minutes. The control samples were pressurized with nitrogen-oxygen mixture (90 pounds per square inch nitrogen; 10 pounds per square inch oxygen). Then the pressure chambers were put on stands in a styrofoam container over liquid nitrogen for gradual cooling for 15 minutes. During cooling down the pressurized chambers in liquid nitrogen vapor, the pressure dropped due to gas contraction and minor leakage. Subsequently the pressure chambers were immersed in liquid nitrogen for another 15 minutes.

The pressure chambers with whole murine hearts were warmed at room temperature for 15 minutes and opened. The temperature of the samples was measured using Sper Scientific 800024 Multi-input Thermocouple Thermometers (Cat. #K-9446I-35 from Cole-Parmer Instrument Company, Vernon Hills, Ill.) with the flexible TeflonR-insulated-wire probe. The temperature of the cardiac samples was −94±2.5° C. just after opening the chamber.

The hardness of the cardiac tissue in the chamber filled with xenon-oxygen mixture under pressure was different in comparison with control cardiac samples which were straight frozen in liquid nitrogen. The cardiac samples were firm and were easily cut with a blade, but not stone-hard as in a control sample, which was straight frozen in liquid nitrogen under normal pressure conditions.

To investigate the extent of the damage of the cardiac tissue after application of the method of the invention involving colder than freezing storage, (based on using a clathrate inducing gas of xenon and oxygen) and the controls frozen under the pressurized nitrogen-oxygen mixture, transmission electron microscopy of the cardiac tissue was performed.

The heart tissue specimens (3×3×3 mm) were cut from the apex and immediately fixed in cold (+4° C.) 2.5% glutaraldehyde in 0.1M Sorensen's sodium buffer (Electron Microscopy Sciences; Cat. #15980) (the cardiac samples were thawed at room temperature to 0° C. before putting them in a fixative to avoid any fixation artifacts). Samples were post-fixed with 1% osmium tetroxide in the same buffer for one hour at room temperature, and then washed three times with the same buffer and three times with distilled water. Samples were stained en bloc with 0.5% uranyl acetate for two hours at room temperature, then washed three times with distilled water and gradually dehydrated with ethanol before being transferred to acetone. Spurr's epoxy resin was used for infiltration and blocks were polymerized for 48 hours at 60° C. Thin-sections were cut on a LEICA Ultracut R microtome and post-stained with uranyl acetate and lead citrate. Samples were observed and recorded at 80 kV accelerating voltage on a Philips CM-12 Scanning Transmission Electron Microscope (the Netherlands) at the Electron Microscopy and W. M. Keck Bioimaging Laboratory at Arizona State University. Images were recorded digitally on a Gatan 791 charge-coupled device camera (Gatan, Inc., Warrendale, Pa.).

Electron microscopy of the cardiac tissues showed obvious and significant differences in the cardiomyocytes' mitochondria structures from the different cryopreservation protocols. There was the presence of irreversible cellular membrane damage (such as disruption of myofibrils and cytoplasmic membrane invaginations) of the cardiac myocytes that were straight frozen in liquid nitrogen under normal pressure. Furthermore, there was decreased density of the mitochondrial matrix in cardiomyocytes cryopreserved with the high pressure nitrogen-oxygen gas mixture and cooled in liquid nitrogen. By contrast, relatively well-preserved mitochondria were present in cardiac myocytes of the cardiac samples after using the method of the invention.

Comparative analysis of structural changes in mitochondria revealed a strong diminution in density of the mitochondrial matrix in the cardiac samples which were straight frozen in liquid nitrogen, compared with the treated cardiac samples. Densitometry of the mitochondrial matrix was performed using lmagej software (NIH; http://rsb.info.nih.gov/ij/). Density of the mitochondrial matrix in mitochondria was normalized against the ribosomes of the rough endoplasmic reticulum. Statistical analysis was done by Student's t-test; values are mean±Standard Deviation (S.D.). A p-value of less than 0.05 was considered statistically significant. The density of the mitochondrial matrix in the cardiac samples hypothermically preserved using a clathrate inducing gas of xenon and oxygen was much higher (almost like in the intact cardiac tissue) than in cardiomyocyte mitochondria in the samples that were frozen in the pressurized nitrogen-oxygen mixture. A p-value of less than 0.05 indicated a statistically significant difference between the densities observed in the samples hypothermically preserved using a clathrate inducing gas of xenon and oxygen according to the invention, compared with the samples frozen in the pressurized nitrogen-oxygen mixture. Approximately 76% of mitochondria of the cardiac samples that underwent hypothermic preservation process of the invention had the same density as the reference cardiac samples. The structure of capillary endothelial cells was relatively well preserved after employing the method of the invention involving below freezing storage.

No mitochondrial swelling, rupture of inner and outer membranes, or leakage of mitochondrial matrix into the cytoplasm was observed in the tissue samples that underwent hypothermic preservation according to the process of the invention. In the control cardiac samples (after straight freezing under high pressure in nitrogen-oxygen mixture at 100 pounds per square inch), electron microscopy demonstrated fragmentation of the mitochondrial inner membrane, rupture of inner and outer membranes, and leakage of mitochondrial matrix into the cytoplasm.

Electron microscopy showed diffuse endothelial cell damage and marked perivascular space edema in the cardiac samples after straight freezing in liquid nitrogen under normal pressure. Extensive capillary damage was in cardiac tissue after incubation at high-pressure nitrogen-oxygen gas mixture and cooling in liquid nitrogen as well. By contrast, the structure of capillary endothelial cells was relatively well preserved after following the hypothermic preservation process of the invention.

Hypothermic preservation of tissue with xenon-oxygen hydrate clathrates may protect tissues by retention of water inside the cells by clathrate formation of the water with the introduced gases, limiting the formation of ice outside the cells. Xenon forms clathrates above 0° C. under relatively low pressure.

Xenon has high skin permeability. Using xenon under high pressure (which is highly permeable) may prevent cells from freezing damage caused by intracellular dehydration. The use of a high pressure xenon-oxygen mixture, according to the invention, resulted in the absence of the following cellular damage: mitochondrial swelling; rupture of inner and outer membranes; and, leakage of mitochondrial matrix into the cytoplasm. In contrast, freezing under high nitrogen pressure exhibited such cellular damage. Others have demonstrated that loss of mitochondrial membrane potential leads to mitochondrial swelling and it is well known that permanent ischemia causes loss of matrix density, and this is associated with mitochondrial swelling.

Another important sign of severe cellular damage is invagination of the cytoplasmic membrane. This was seen in our control cardiac samples after straight freezing in liquid nitrogen. This morphologic finding indicates membrane damage.

Mitochondrial volume homeostasis is a housekeeping function that is essential for maintaining the structural integrity of the organelle. Mitochondrial swelling is also one of the key players in cytochrome c release associated with apoptotic cell death. Measurement of the concentration of cardiolipin may be done to assess mitochondrial damage. In intact cells, the cellular distribution of cardiolipin is restricted to mitochondria. The detection of cardiolipin outside of mitochondria is a sign of severe mitochondrial membrane damage. Intercellular freezing can cause cellular damage in the course of thawing, during which re-crystallization can occur. In contrast, xenon gas hydrate clathrates formed according to the invention are easily broken as the pressure drops, without intracellular water re-crystallization.

EXAMPLE 2

Recovered Biological Tissue Having a Biopreservation Marker

In an embodiment, a recovered biological tissue sample, previously hypothermically preserved at a temperature of between −10° C. and −20° C., has a temperature of at least +50° C. and exhibits metabolism. The recovered biological tissue preferably has a biopreservation marker in a measureable quantity. The measureable quantity of the biopreservation marker may be distinct from a quantity in the biological tissue exhibiting metabolism prior to hypothermic preservation. For example, the biopreservation marker may be cardiolipin or lactate dehydrogenase.

EXAMPLE 3

Recovery of Hypothermically Preserved Tissue without Recompression

The solubility characteristics of the clathrate-forming gas used in hypothermically preserving the tissue may affect the amount of gas dissolved in the sample. For example, sulfur hexafluoride has a lower solubility in biological tissue than xenon. When tissue hypothermically preserved with xenon is warmed without flushing and repressurization with a gas such as a helium-oxygen mixture, bubbles of xenon gas can form in the tissue, and can cause damage to the tissue.

In contrast, because of the lower solubility in biological tissue of sulfur hexafluoride, tissue hypothermically preserved with sulfur hexafluoride may be warmed without flushing and repressurization without the formation of sulfur hexafluoride bubbles in the tissue for a broader range of conditions of the hypothermically preserved tissue (e.g., range of temperature of hypothermic preservation and/or pressure of clathrate-forming gas imposed on the tissue during hypothermic preservation).

EXAMPLE 4

Formation of Xenon Hydrate Clathrates in Animals

Trials were performed in which a gaseous mixture including xenon (about 90 mol %), nitrogen (about 8 mol %), and oxygen (about 2 mol %) at a total pressure of about 50 pounds per square inch was imposed on live Planaria organisms at a temperature of +50° C. Xenon clathrate formation in the tissues of the Planaria was observed. The high-pressure container in which the Planaria were held included a glass window as an observation port. Through the observation port, a change in color of the Planaria tissue to a cotton-like appearance was indicative of the formation of xenon clathrate hydrate; the appearance was distinct from that of frozen tissue in which intracellular ice has formed. Moreover, an observed cessation of movement of the Planaria organisms was associated with the formation of xenon clathrate hydrate in tissue.

After the pressure was released and the Planaria were returned to air at atmospheric pressure, the xenon clathrate hydrate observed in the tissue of the Planaria was observed to have dissipated; a change in color of the Planaria tissue was observed. Furthermore, after the pressure was released and the Planaria were returned to air at atmospheric pressure, the Planaria were observed from their movement to be alive and survived for about 24 hours. This indicated that the procedure of forming xenon clathrate hydrates in Planaria was reversible, and that Planaria hypothermically preserved through the formation of xenon clathrate hydrates were viable.

EXAMPLE 5

Formation of Sulfur Hexafluoride Hydrate Clathrates in Animals

Trials were performed in which a gaseous mixture of sulfur hexafluoride at a partial pressure of 90 pounds per square inch and oxygen at a partial pressure of 10 pounds per square inch (for a total pressure of 100 pounds per square inch) was imposed on live Planaria organisms. The Planaria organisms under the gaseous mixture were cooled on ice to a temperature of about 0° C. Sulfur hexafluoride clathrate formation in the tissues of the Planaria was observed. The high-pressure container in which the Planaria were held included a glass window as an observation port. Through the observation port, a change in color of the Planaria tissue to a cotton-like appearance was indicative of the formation of sulfur hexafluoride clathrate hydrate; the appearance was distinct from that of frozen tissue in which intracellular ice has formed. Moreover, an observed cessation of movement of the Planaria organisms was associated with the formation of sulfur hexafluoride clathrate hydrate in tissue.

After the pressure was released and the Planaria were returned to air at atmospheric pressure, the sulfur hexafluoride clathrate that had been observed in the tissue of the Planaria was observed to have dissipated; a change in color of the Planaria tissue was observed. Furthermore, after the pressure was released and the Planaria were returned to air at atmospheric pressure, the Planaria were observed from their movement to be alive and survived for about 24 hours. This indicated that the procedure of forming sulfur hexafluoride clathrates in Planaria was reversible, and that Planaria hypothermically preserved through the formation of sulfur hexafluoride clathrate hydrates were viable.

EXAMPLE 6

Hypothermic Preservation of Animals with Sulfur Hexafluoride or Xenon Hydrate Clathrates and Recovery A clathrate-forming gas, e.g., sulfur hexafluoride and/or xenon, may be used to reversibly hypothermically preserve organisms and animals. For example, a clathrate inducing gas under pressure, e.g., a mixture of sulfur hexafluoride at a partial pressure of about 90 pounds per square inch and oxygen at a partial pressure of about 10 pounds per square inch (for a total pressure of 100 pounds per square inch) or a mixture of xenon at a partial pressure of about 90 pounds per square inch and oxygen at a partial pressure of about 10 pounds per square inch (for a total pressure of 100 pounds per square inch), may be imposed on an organism such as an animal, e.g., Planaria, in a high-pressure chamber. The high-pressure chamber with the organism, e.g., Planaria, may be cooled on ice for about 1 hour, say, to a temperature approaching 0° C. The high-pressure chamber with the organism, e.g., Planaria, can then be cooled to a temperature of about −20° C., the pressure of the clathrate inducing gas may be released, and the organism, e.g., Planaria, in the high-pressure chamber may be exposed to air in the atmosphere. The high-pressure chamber with the organism, e.g., Planaria, may be maintained as hypothermically preserved at −20° C. for an extended period of time, for example, one week.

The hypothermically preserved organism, e.g., Planaria, can then be recovered, for example, as follows. The high-pressure chamber with the organism, e.g., Planaria, may be flushed with a mixture of an inert gas and oxygen, for example, with helium at a partial pressure of about 90 pounds per square inch and oxygen at a partial pressure of about 10 pounds per square inch, to remove the clathrate forming gas, e.g., sulfur hexafluoride and/or xenon, from the biological tissues of the animal. The temperature of the high-pressure chamber with the organism, e.g., Planaria, can then be gradually increased with time, for example, to room temperature, e.g., about +20° C. As the temperature is increased, the pressure may be gradually decreased. Such flushing followed by gradual warming and depressurization may be used to avoid the formation of gas bubbles in the organism that could be harmful to tissue. The organism, e.g., Planaria, can then be removed from the chamber and exposed to air at atmospheric pressure and room temperature. The state of the organism, for example, its life functions, may be investigated.

EXAMPLE 7

Hypothermic Preservation of Animal Organs with Sulfur Hexafluoride or Xenon Hydrate Clathrates and Recovery A clathrate-forming gas, e.g., sulfur hexafluoride and/or xenon, may be used to reversibly hypothermically preserve whole organs or parts of organs from animals. For example, a clathrate inducing gas under pressure, e.g., a mixture of sulfur hexafluoride at a partial pressure of about 90 pounds per square inch and oxygen at a partial pressure of about 10 pounds per square inch (for a total pressure of 100 pounds per square inch) or a mixture of xenon at a partial pressure of about 90 pounds per square inch and oxygen at a partial pressure of about 10 pounds per square inch (for a total pressure of 100 pounds per square inch), may be imposed on an organ such as a heart, kidney, or liver. The high-pressure chamber with the organ may be cooled on ice for about 1 hour, say, to a temperature approaching 0° C. The high-pressure chamber with the organ can then be cooled to a temperature of about −20° C., the pressure of the clathrate inducing gas may be released, and the organism, e.g., Planaria, in the high-pressure chamber may be exposed to air in the atmosphere. The time for cooling the organ and releasing the pressure may be varied, depending, for example, on the size of the organ. For example, a small organ sample, e.g., some cells, may require less than 24 hours. For example, a whole internal organ, such as a heart, kidney, or liver, may require as much as 48 hours or 72 hours. The high-pressure chamber with the organ may be maintained as hypothermically preserved at −20° C. for an extended period of time, for example, one week.

The hypothermically preserved organ can then be recovered, for example, as follows. The high-pressure chamber with the organ may be flushed with a mixture of an inert gas and oxygen, for example, with helium at a partial pressure of about 90 pounds per square inch and oxygen at a partial pressure of about 10 pounds per square inch, to remove the clathrate forming gas, e.g., sulfur hexafluoride and/or xenon, from the biological tissues of the organ. The temperature of the high-pressure chamber with the organ can then be gradually increased with time, for example, to room temperature, e.g., about +20° C. As the temperature is increased, the pressure may be gradually decreased. Such flushing followed by gradual warming and depressurization may be used to avoid the formation of gas bubbles in the organ that could be harmful to tissue. The organ, e.g., heart, kidney, or lung, can then be removed from the chamber and exposed to air at atmospheric pressure and room temperature. The viability of the organ, for example, its metabolism, may be investigated. Such a procedure of hypothermically preserving and then recovering an organ could be useful, for example, in human organ transplantation procedures.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The above-described embodiments including the drawings are examples of the invention and merely provide illustrations of the invention. Other embodiments will be obvious to those skilled in the art. Thus, the scope of the invention is determined by the appended claims and their legal equivalents rather than by the examples given.

INDUSTRIAL APPLICABILITY

The invention may be used in the medical industry to store human blood components for transfusion, such as human blood platelets, and human organs for transplantation, such as hearts, kidneys, and livers. The invention may also be used in the food industry for high-quality preservation of food, such as seafood.

What is claimed is:

1. A method for hypothermic preservation of biological tissue for later recovery to a viable state, comprising the steps of:
   (a) in a closed environment, flushing a biological tissue with a clathrate inducing gas mixture consisting of a clathrate inducing gas and oxygen, wherein the clathrate inducing gas is selected from the group consisting of: sulfur hexafluoride and xenon, wherein the clathrate inducing gas is in a concentration in the clathrate inducing gas mixture within a range of about 75 mole percent to 95 mole percent, wherein said flushing displaces gases surrounding the biological tissue with the clathrate inducing gas mixture;
   (b) pressurizing the flushed biological tissue and the resultant surrounding clathrate inducing gas mixture of step (a) to a pressure of 100 psig to form clathrates inside the biological tissue of step (a) at a first temperature in a range of 1° C. to 5° C.; and
   (c) cooling the biological tissue and the surrounding clathrate inducing gas mixture of step (b) to a second temperature of −20° C.

2. The method of claim 1 further comprising the steps of:
   (d) adjusting the pressure and temperature of the cooled biological tissue and the surrounding clathrate inducing gas mixture of step (c) to between about 15 psig to 100 psig and between −20° C. to −10° C. respectively.

3. The method of claim 2, wherein the pressure of step (d) is approximately 15 pounds psig.

4. The method according to claim 2, further comprising the steps of:
   (e) flushing the biological tissue and the surrounding clathrate inducing gas mixture of step (d) with a recovery gas mixture consisting of:
   helium in a concentration within a range of 90 mole percent to 95 mole percent and oxygen in a concentration within a range of about 5 mole percent to 10 mole percent, wherein said flushing of step (e) displaces the clathrate inducing gas mixture surrounding the biological tissue with the recovery gas mixture;
   (f) subjecting the biological tissue and the resultant surrounding recovery gas mixture of step (e) a recovery pressure of between about 75 psig and 100 psig;
   (g) warming the biological tissue and the surrounding recovery gas mixture of step (f) to a first recovery temperature above 0° C.; and
   (h) depressurizing and warming the biological tissue and the surrounding recovery gas mixture of step (g) to a pressure and temperature that restores the biological tissue of step (g) to a viable state.

5. The method of claim 1, wherein step (b) is performed approximately isothermally.

6. The method of claim 1, wherein step (c) is performed approximately isobarically.

7. The method according to claim 1, further comprising the steps of:
   (d) flushing the biological tissue and the surrounding clathrate inducing gas mixture of step (c) with a recovery gas mixture consisting of:
   helium in a concentration within a range of 90 mole percent to 95 mole percent and oxygen in a concentration within a range of about 5 mole percent to 10 mole percent, wherein said flushing of step (d) takes place at a pressure within a range of 100 psi absolute to 120 psig absolute to yield a biological tissue surrounded by the recovery gas mixture; and
   (e) depressurizing and warming the biological tissue and the surrounding recovery gas mixture to a pressure and temperature that restores the biological tissue to a viable state.

8. The method according to claim 1 wherein the clathrate-inducing gas is sulfur hexafluoride, and further comprising the step (d) of depressurizing and warming the biological tissue and the surrounding clathrate inducing gas mixture of step (c) to a pressure and temperature that restores the biological tissue of step (c) to a viable state; wherein the rate of warming is sufficient to preclude formation of sulfur hexafluoride bubbles in the biological tissue of step (c).

* * * * *